United States Patent [19]

Ingebrigtsen et al.

[11] Patent Number: 5,085,221
[45] Date of Patent: Feb. 4, 1992

[54] ULTRASONIC IMAGING PROBE

[75] Inventors: Kjell A. Ingebrigtsen, Trondheim, Norway; William C. Aurand, Lewistown, Pa.

[73] Assignees: Interspec, Inc., Ambler, Pa.; Vingmed Sound A/S, Norway

[21] Appl. No.: 538,109

[22] Filed: Jun. 14, 1990

[51] Int. Cl.$^5$ .............................................. A61B 8/12
[52] U.S. Cl. ................. 128/660.1; 128/662.06; 73/633
[58] Field of Search ........... 128/660.01, 660.1, 662.06, 128/24 A; 73/633

[56] References Cited

U.S. PATENT DOCUMENTS

| | | | |
|---|---|---|---|
| 4,494,549 | 1/1985 | Namba et al. | 128/662.06 |
| 4,545,386 | 10/1985 | Hetz et al. | 128/662.06 |
| 4,817,616 | 4/1989 | Goldstein | 128/662.06 |
| 4,869,257 | 9/1989 | Molnar et al. | 128/662.06 |
| 4,972,839 | 11/1990 | Angelsen | 128/660.1 X |

Primary Examiner—Francis Jaworski
Attorney, Agent, or Firm—Ratner & Prestia

[57] ABSTRACT

A transesophageal echo cardiography probe includes a cylindrical housing (1) and end cap (2), a rotatable axle (10) extending longitudinally along the housing, a motor (7) operable for rotating the axle (10), and a multielement ultrasonic transducer array (5) carried on and for rotation with said axle (10) for emitting an ultrasonic imaging beam. The array elements (5A) are connected to a flexible, first flat cable (11) that extends, preferably in an S-like undulating manner, radially-outwardly toward the end cap wall. The radially-outward end of the first cable (11) is connected to a second flat cable (12) which extends longitudinally along the housing (1) to the rearward end of the housing. The second cable (12) has an arcuate cross-sectional shape for facilitating its receipt in and extension through an arcuate passageway defined between the motor (7) and the inner periphery of the housing (1).

20 Claims, 4 Drawing Sheets

ULTRASONIC IMAGING PROBE

FIELD OF THE INVENTION

The present invention relates to an ultrasonic scanning probe which is particularly adapted for use in transesophageal echo cardiography. In particular the invention is directed to an ultrasonic transducer array probe for image scanning in such applications in arbitrary selected sector planes within a threedimensional space.

BACKGROUND OF THE INVENTION

Various types of ultrasonic scanners for cardiac studies are well known. Such scanning probes are disclosed, by way of example, in U.S. Pat. Nos. 4,543,960 and 4,841,979, and in published European patent application No. 039.045.

U.S. Pat. No. 4,543,960 discloses an ultrasonic transesophageal echo cardiography probe including a transducer array consisting of a number of transducer elements and rotatable about an axis having an orientation normal to the general plane of the transducer array. The mechanical rotation of the array in this arrangement is performed manually for the purpose of selecting desired scan or sector planes. Thus, no combination of motor-driven mechanical and electronic scanning is contemplated. The devices of U.S. Pat. No. 4,841,979 and published European patent application No. 039.045, on the other hand, employ a simple transducer and no transducer array. Both of these publications describe a rotary movement of the transducer, as well as the possibility of additional movement components, so as to cover a region in space.

A probe for image scanning into orthogonal sector planes from the esophagus has also been proposed. The probe uses two separate phased array transducers for obtaining such scanning. This solution, however, has obvious drawbacks in that each of the two transducer arrays must be independently connected by a large number of independent electrical leads. Moreover, the two arrays must of necessity be located in physcially different positions, resulting in different centers of the two orthogonal scan sectors. Thus, a direct comparative reference between the images and the Doppler velocity measurements from the two scan planes is difficult to obtain. The use of two independent transducer arrays also substantially increases the size of the probe, a highly undesirable and often unacceptable condition for carrying out cardiac imaging from the esophagus.

SUMMARY OF THE INVENTION

It is accordingly an object of the present invention to provide an ultrasonic probe, useful for diagnostic purposes and, in particular, for transesophageal echo cardiography, based on a simpler solution than is available with, and overcoming those difficulties and drawbacks associated with, heretofore-known probes.

Thus, and in accordance with the present invention, the new and improved ultrasonic probe includes a substantially cylindrical housing provided with a rounded end cap, a multielement ultrasonic transducer array in which a number of generally longitudinal transducer elements are arranged in substantially parallel, side by side, relation, a rotatable axle carrying the transducer array and oriented transverse to the main direction of ultrasonic emission from the transducer array, drive means for rotating the rotatable axle and arranged substantially centrally within the cylindrical housing, a flexible first flat cable formed of a plurality of electrical conductors necessary for the operation of the transducer array and extending generally radially outward from a region proximate the rotatable axle toward the inner periphery or side wall of the end cap, and a second flat cable containing at least a corresponding number of conductors to that of the first flat cable and extending in the longitudinal direction of the housing, the second cable having an arcuate cross-sectional shape so as to facilitate its passage in an arcuate space defined between the centrally-arranged drive means and the inner periphery or side wall of the housing.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein similar reference characters denote similar elements through the several views.

DETAILED DESCRIPTION OF THE PREFERRED EMBODIMENT

Figure 1:
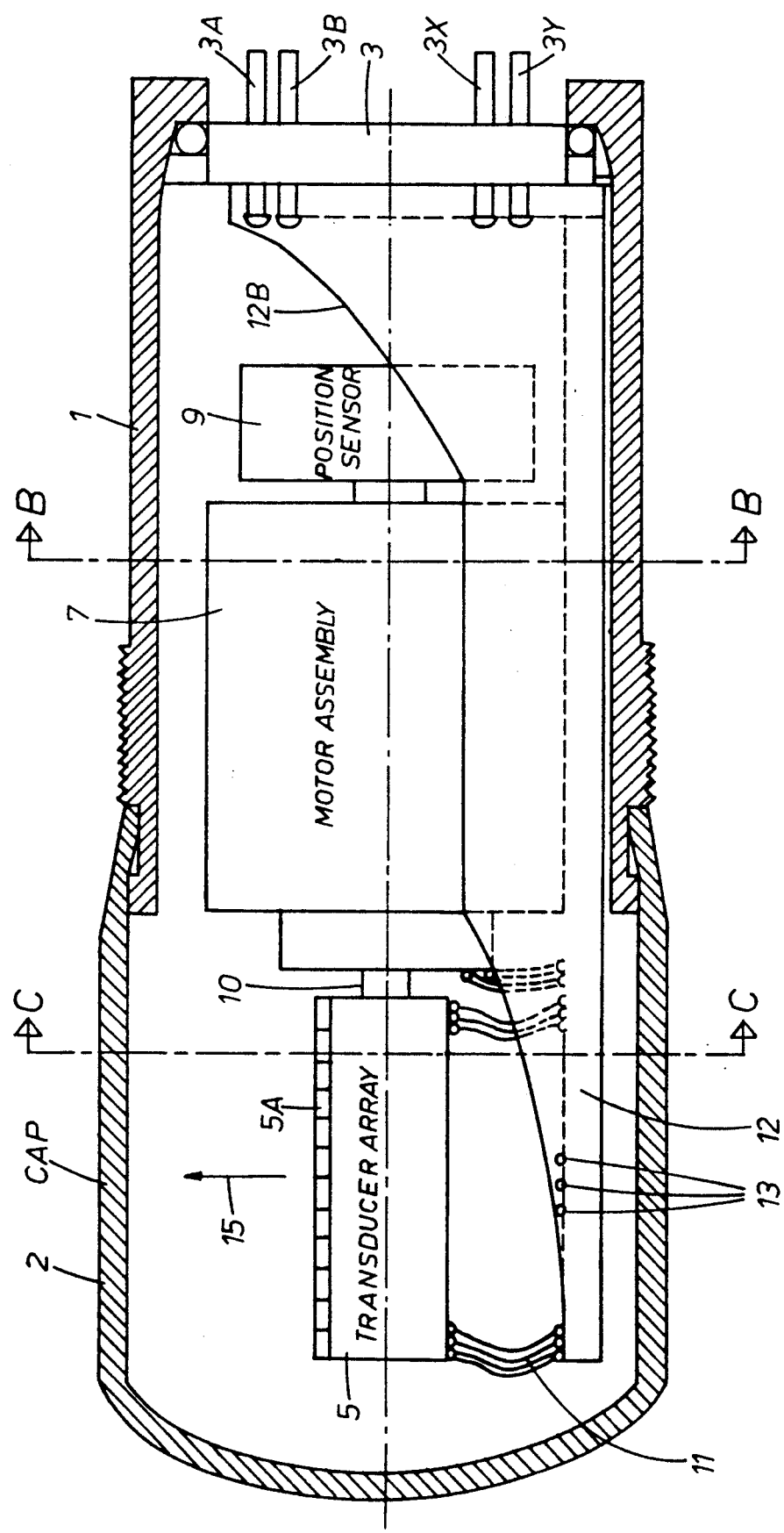
FIG. 1 is a side view, in axial section, through a probe constructed in accordance with the teachings of the present invention.
Figure 2:
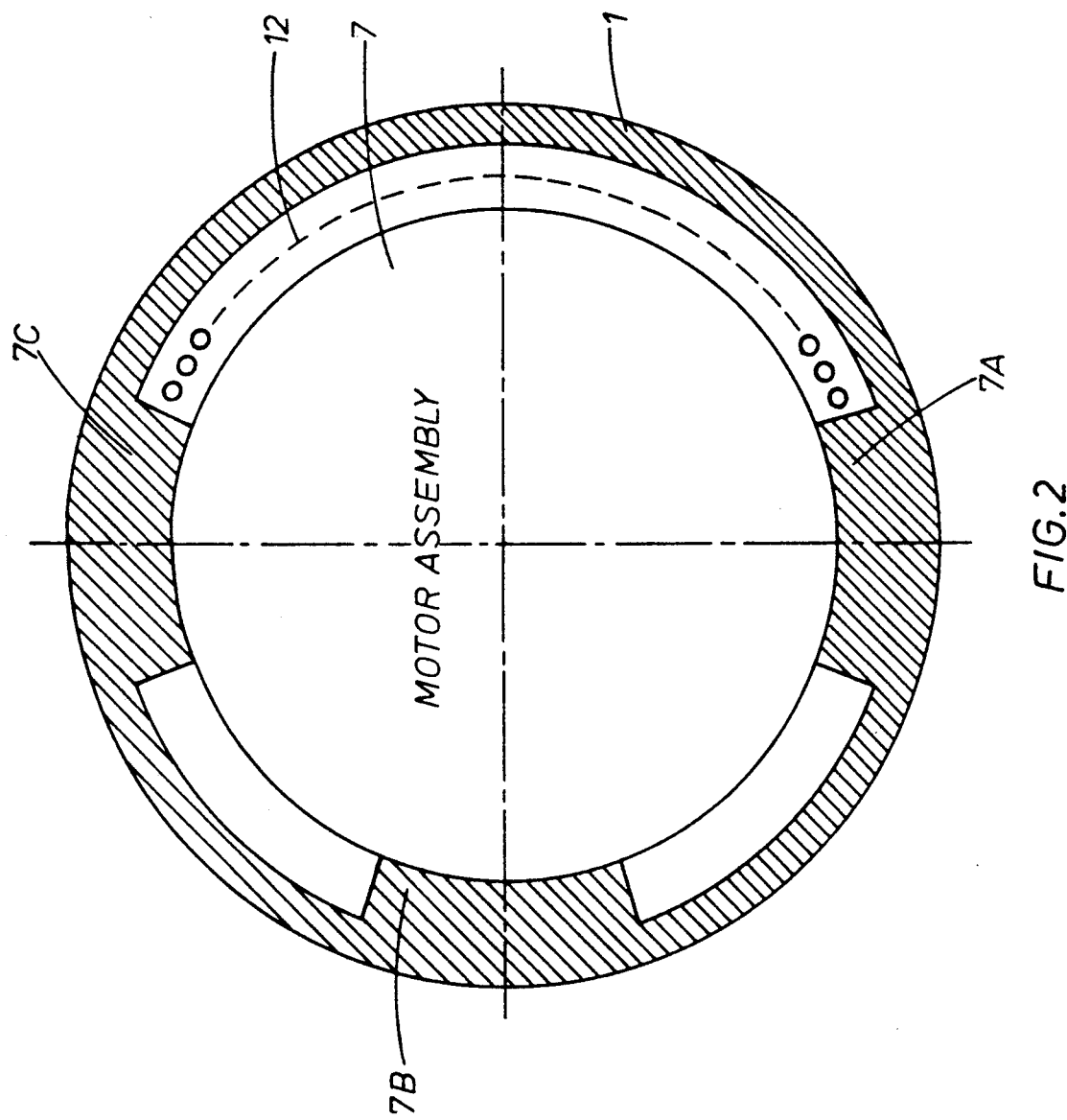
FIG. 2 is a cross-section taken along the lines B—B in FIG; 1.
Figure 3:
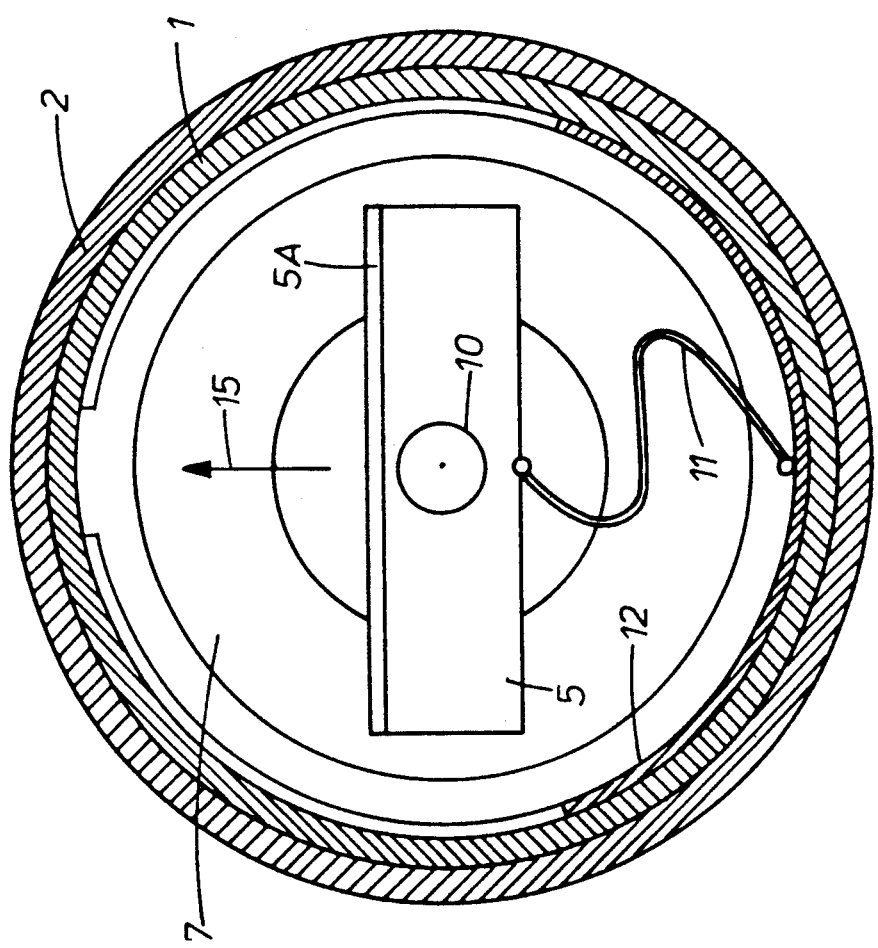
FIG. 3 is a cross-section taken along the lines C—C in FIG. 1.

The probe shown in FIGS. 1, 2 and 3, which probe is constructed in accordance with the present invention, comprises a cylindrical and generally elongated motor housing 1 and an end cap 2 attached to the housing and formed at least in part of a material which is substantially transparent to ultrasonic waves. At the end of the probe opposite the cap 2 the housing 1 is closed by a plug or cover 3 through which there extend a plurality of contact pins 3A, 3B ... 3X, 3Y for effecting electrical connections between external operating and/or monitoring apparatus (not shown) for the probe, on the one hand, and a transducer array 5, motor assembly 7 and position sensor assembly 9 disposed within the probe housing and end cap, on the other. A suitable ultrasonically-transmissive liquid filling is normally provided within the housing 1 and cap 2.

In this disclosed and currently preferred embodiment of the invention the motor 7, the transducer array 5 and the position sensor 9 are all provided with or carried on a common rotatable axle 10 which runs substantially centrally and axially through the elongated motor housing 1 and end cap 2. For this purpose the motor 7 may include an output axle connected directly to the rotatable axle 10 so that, with operation of the motor 7, the resulting rotation of the output axle is transferred directly to the axle 10 for driven rotation of the axle 10.

The transducer array 5 is formed of a multiplicity of elongated transducer elements 5A seen endwise in FIG.

1 and having the general or main direction of ultrasound wave emission indicated by the arrow 15 in FIGS. 1 and 3. Thus, the transducer elements 5A are oriented with their longitudinal elongations extending substantially transverse to the rotatable axle 10. As should be apparent, through suitable excitation of the transducer elements forming the transducer array 5 the direction of the emitted ultrasound beam may be varied, from the main or central direction 15, within a predetermined angular range, i.e. at varying angles to the longitudinal axis of the probe which, as seen in FIG. 1, corresponds to the axis of the rotatable axle 10.

In an optional modification of the arrangement shown in FIGS. 1, 2 and 3, the axis of rotation of the transducer array 5 may be oriented substantially transverse to the longitudinal axis of the housing 1 and cap 2, using a suitable form of drive means such, for example, as pullies and wire, to effect the required rotational movement of the transducer array. In that case the main direction of ultrasound emission would be endwise from the probe cap—i.e. along or substantially parallel to the longitudinal axis of the probe. The modified form of array drive means in such an arrangement would also be disposed substantially centrally within the housing 1 as in the preferred embodiment specifically described and illustrated herein.

A serious problem in multielement array probes of the general type herein disclosed lies in the provision of an orderly and practical arrangement of the numerous electrical conductors or leads which must necessarily extend from the comparatively large number of transducer elements—these elements being operatively subjected to rotary or swinging movements—to equipment outside or externally of or otherwise remote from the probe itself. As shown in FIGS. 1 and 3, in accordance with the present invention a flexible first and ribbon-like lead or flat cable 11 is provided between the back or non-emitting side of the transducer array 5—i.e. opposite the ultrasonic beam emission direction indicated by the arrow 15—and a second flat cable or conductor adaptor 12 extending in the longitudinal direction of the cap 2 and housing 1 adjacent the inner peripheral circumference thereof. The flexible first flat cable 11 extends generally radially outward within the end cap 2 from a region proximate the rotatable axle 10. The length of the cable 11 is preferably well in excess of the radial distance across which it extends—i.e. between the back or rear or nonemission side of the transducer array 5 and the connection to the second cable 12 —thereby forming S-like undulations or folds or a generally corrugated configuration so as to permit and accomodate the required rotational movements of the transducer array 5 without placing undue stress or strain on the flat cable 11 or on the connections thereto at its opposite ends.

Figure 4:
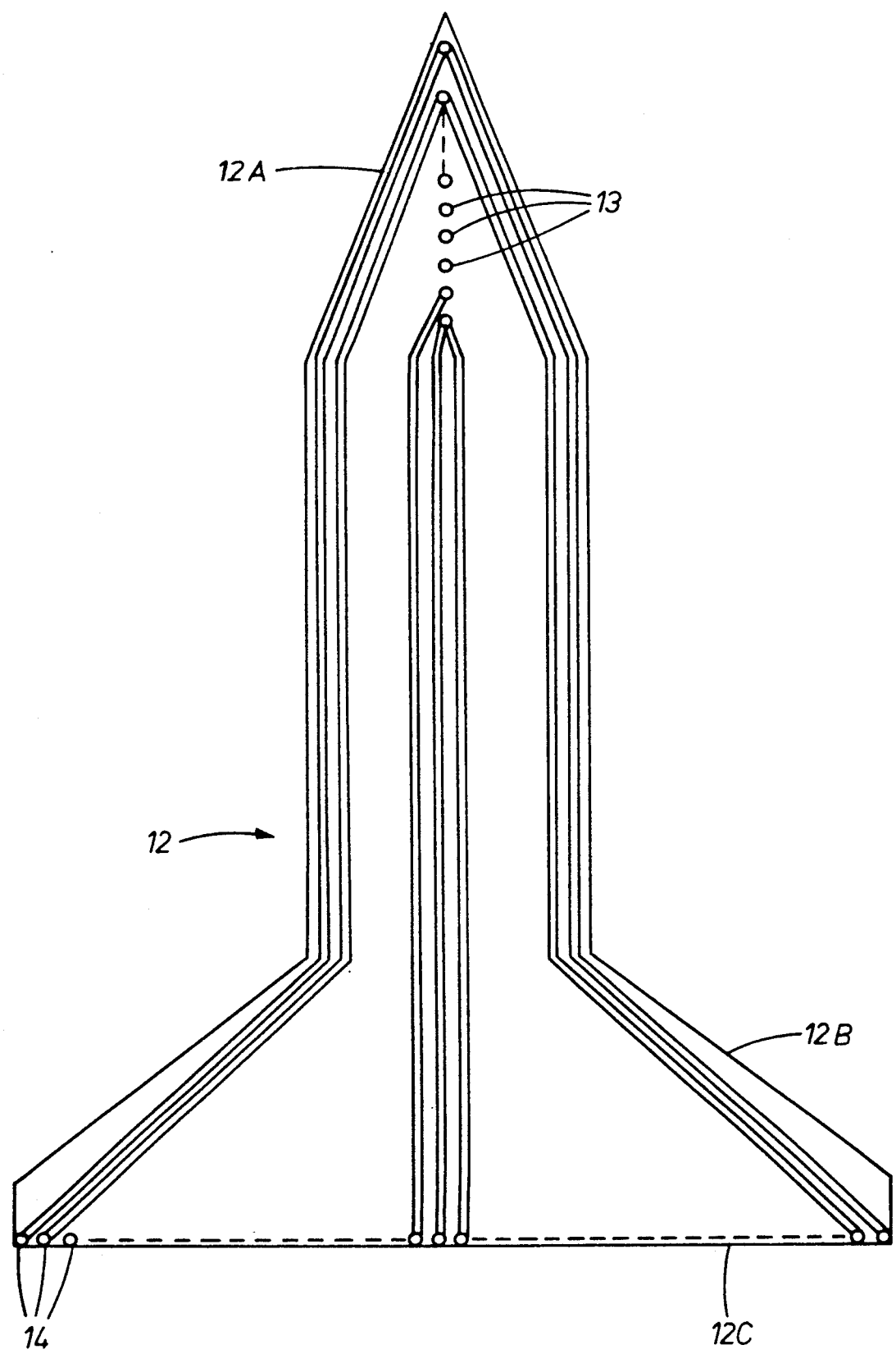
FIG. 4 illustrates one form of a flat cable or printed circuit lead arrangement in accordance with the invention for use in the probe of FIGS. 1, 2 and 3.

Provided at the forward or lefthand (in FIG. 1) end of the second flat cable, i.e. proximate the transducer array 5 and first flat cable 11, is a row or series of connecting points 13 between the individual conductors in the first flat cable 11 and the corresponding conductors in the second flat cable 12. The arrangement of these connecting points 13 is most clearly seen in FIG. 4, which also depicts a tapered portion 12A of the second flat cable 12 in this forward end region thereof. The electrical connections between the first and second cables 11, 12 at the points 13 may be effected by soldering or bonding or in any other suitable manner as a matter of design choice.

As shown in FIG. 2, the motor assembly 7 is mounted within the motor housing 1 by means of a plurality of mounting pieces or spacers or brackets 7A, 7B, 7C. The preferred arrangement of these brackets provides, as between the brackets 7A and 7C, a sufficiently wide angular space for accommodating therein the second flat cable 12 which may advantageously have an arcuate cross-sectional configuration for facilitating the cable's longitudinal passage or extension through this space between the interior periphery of the housing 1 and the outer periphery of the motor 7. At the inner or rear or righthand (in FIG. 1) end of the probe the second flat cable 12 has a widened region 12B (FIG. 4) so that the terminating end of the cable 12 at its widened edge 12C may extend about substantially the entire inner circumference of the housing 1 for ready and convenient connection to the contact pins 3A, 3B . . . 3X, 3Y which extend through the end plug 3.

With the arrangement of conductors and connections herein disclosed in accordance with the invention it is possible to provide for an unusually large number of conductors within and through the probe, while enabling the probe to be fabricated having optimally or suitably minimized dimensions appropriate for its intended utility and manner of use.

In further accordance with the invention, the flat or ribbon cables 11, 12 may comprise any suitable form of flat electronically-conductive leads such, for example, as printed circuit conductors carried on a flexible substrate or the like. In particular, while the first flat cable 11 must be flexible, the second flat cable 12 may be flexible but need not be so fabricated. The second cable 12 must, however, at least be capable of being configured or shaped so as to pass, in the axial or longitudinal extension of the probe, at least closely proximate the inner circumferential or peripheral wall of the end cap 2 and housing 1, thereby leaving a substantially unencumbered central space or volume within the probe for accommodating the required drive means—such, for example, as the motor assembly 7—as well as the position sensor assembly 9 and/or other components.

Using a probe as herein described, electronic scanning of the ultrasonic beam can be effected in a sector plane which coincides with the mechanical rotational axis. In addition, mechanical scanning can be carried out in a sector plane normal to the mechanical rotational axis, effected by operation of the motor 7 with the position sensor 9 enabling selective positioning of the electronic scan plane at an accurate angle in any location within a sector of, typically, 90°. Likewise, by positioning the beam at an arbitrary angle relative to the rotational axis through electronic beam steering, the mechanical scan plane can have an arbitrary angle within a 90° sector relative to the rotational axis. Thus, two independent orthogonal scan planes are covered or established.

A necessary prerequisite for realizing the intended mechanical rotation of the transducer array is the provision of a flying lead configuration—or functionally equivalent structure —for implementing the connections to the transducer array elements. In accordance with the present invention, these connection requirements are met by the flat cable arrangements heretofore described, as for example employing flexible printed circuit-like connections.

By synchronizing the mechanical and the electronic scan components, an arbitrarily-located scan plane may be selected and, with the respective mechanical and electronical scan velocities being substantially constant (i.e. independent of time), the resulting scanned surface will be planar. This may be particularly advantageous for examinations from the esophagus where it is desirable to keep the probe in a fixed position and, from that position, to adjust the image plane in order to obtain a better characterization of pathology or for mapping of the coronary arteries.

The beam pointing direction is independently determined by the position sensor 9 and utilizing an electronic computing algorithm (the calculations being carried out in external equipment) which controls the delay settings of the various transducer elements 5A in the array 5. Dynamic focusing may be obtained in the electronic scan plane.

Although the transducer array 5 herein shown and described has a generally rectangular configuration, those skilled in the art will recognize that such a transducer element assembly may alternatively be circular, elliptical or have any other modified or rectilinear shape. Transducer arrays having transducer elements of varying length—also within the intended scope and contemplation of the invention—will influence the effective antenna aperture and, consequently, the emitted ultrasonic beam profile.

Moreover, an electrically-controlled array is capable of simultaneously supporting several "independent" ultrasonic beams. Data collection from blood or tissue examination can thus be accelerated and expedited by parallel processing of different beams. The combination of mechanical scanning and of plural simultaneous ultrasonic beams provided by phase steering of the transducer array provides a unique, practical opportunity for collecting three-dimensional data, in real time, of moving objects such as the heart and the flow of blood with good resolution.

Finally, it should be pointed out that the phased array transducer 5 may be shaped without the emitting surfaces of the individual transducer elements lying in a single plane, as in a linear array transducer, or with other, modified shapes of the total or overall emitting surface so as to substantially depart from a planar configuration, as in a curvilinear array. Such modified surface shapes may, of course, also be combined with rectangular, circular or elliptical transducer arrays as mentioned above. All such modifications are within the intended scope of the invention.

While there have been shown and described an pointed out fundamental novel features of the invention as applied to a currently preferred embodiment thereof, it will be understood that various omissions and substitutions and changes in the form and details of the device illustrated, and in its operation, may be made by those skilled in the art without departing from the spirit of the invention. It is the intention, therefore, to be limited only as indicated by the scope of the claims appended hereto.

What is claimed is:

1. An ultrasonic diagnostic scanning probe, comprising:
   a substantially cylindrical housing (1) having a peripheral wall and a longitudinal axis;
   an end cap (2) mounted on said housing (1) and closing a forward end of the housing, said end cap having an inner periphery;
   a multielement ultrasonic transducer array (5) formed of a plurality of elongated transducer elements (5A) disposed in substantially parallel, side-by-side relation and operable for emitting an ultrasonic beam from said array (5) in a main ultrasonic emitting direction (15);
   an operatively-rotatable axle (10) carrying said transducer array (5) for rotating the array and extending substantially transverse to the elongation of said transducer elements (5A) and to said main ultrasonic emitting direction (15);
   drive means (7) for rotating said rotatable axle (10), said drive means being substantially centrally disposed within said housing (1) and defining a longitudinally-extending, cross-sectionally arcuate passageway between said drive means (7) and said housing peripheral wall;
   a flexible first flat cable (11) comprising a plurality of electrical conductors connected at one end to said transducer array (5), said first cable (11) extending substantially radially outwardly from said array (5) toward and proximate to said end cap inner periphery; and
   a second flat cable (12) comprising a plurality of electrical conductors at least equal in number to said plurality of conductors of said first cable (11), said second cable (12) extending within and along said passageway and substantially parallel to said housing axis, and having an arcuate crosssectional configuration for facilitating accomodation of the second cable (12) in said passageway.

2. An ultrasonic diagnostic scanning probe in accordance with claim 1, wherein said drive means comprises an electrically-operable motor (7) having an output axle connected directly to said rotatable axle (10) for rotating the rotatable axle (10), said output and rotatable axles being disposed substantially centrally within said housing (1) and extending longitudinally along said housing axis.

3. An ultrasonic diagnostic scanning probe in accordance with claim 2, wherein said flexible first flat cable (11) includes a first end proximate said transducer array (5) and a second end proximate said end cap inner periphery, and said first cable (11) extends between its first and second ends in an S-like undulating configuration so as to accomodate rotation of said transducer array (5).

4. An ultrasonic diagnostic scanning probe in accordance with claim 3, wherein the second end of said first flat cable (11) is directly connected to said second flat cable (12) at a plurality of connection points (13).

5. An ultrasonic diagnostic scanning probe in accordance with claim 4, wherein said connection points (13) are arranged in a row extending substantially parallel to the longitudinal axis of said housing (1).

6. An ultrasonic diagnostic scanning probe in accordance with claim 5, wherein said electrical conductors of said second cable (12) have a tapered configuration proximate said connection points (13).

7. An ultrasonic diagnostic scanning probe in accordance with claim 1, wherein said flexible first flat cable (11) includes a first end proximate said transducer array (5) and a second end proximate said end cap inner periphery, and said first cable (11) extends between its first and second ends in an S-like undulating configuration so as to accomodate rotation of said transducer array (5).

8. An ultrasonic diagnostic scanning probe in accordance with claim 7, wherein the second end of said first flat cable (11) is directly connected to said second flat cable (12) at a plurality of connection points (13).

9. An ultrasonic diagnostic scanning probe in accordance with claim 8, wherein said connection points (13)

are arranged in a row extending substantially parallel to the longitudinal axis of said housing (1).

10. An ultrasonic diagnostic scanning probe in accordance with claim 9, wherein said electrical conductors of said second cable (12) have a tapered configuration proximate said connection points (13).

11. An ultrasonic diagnostic scanning probe in accordance with claim 1, wherein said first flat cable (11) is directly connected to said second flat cable (12) at a plurality of connection points (13).

12. An ultrasonic diagnostic scanning probe in accordance with claim 11, wherein said connection points (13) are arranged in a row extending substantially parallel to the longitudinal axis of said housing (1).

13. An ultrasonic diagnostic scanning probe in accordance with claim 12, wherein said electrical conductors of said second cable (12) have a tapered configuration proximate said connection points (13).

14. An ultrasonic diagnostic scanning probe in accordance with claim 2, wherein said first flat cable (11) is directly connected to said second flat cable (12) at a plurality of connection points (13).

15. An ultrasonic diagnostic scanning probe in accordance with claim 14, wherein said connection points (13) are arranged in a row extending substantially parallel to the longitudinal axis of said housing (1).

16. An ultrasonic diagnostic scanning probe in accordance with claim 15, wherein said electrical conductors of said second cable (12) have a tapered configuration proximate said connection points (13).

17. An ultrasonic diagnostic scanning probe in accordance with claim 1, further comprising a connection plug (3) located proximate a rear end of said housing (1) and a plurality of contact pins (3A, 3B . . . 3X, 3Y) carried on said plug (3), and said second flat cable having a width, a forward end located prximate said first cable (11), a central portion extending through said passageway, and a rearward end located proximate said housing rear end and including a terminating edge (12c) carrying contact points (14) connected to said contact pins, said second cable rearward end having a width greater than said second cable central portion.

18. An ultrasonic diagnostic scanning probe in accordance with claim 17, wherein said second cable rearward end has a width that gradually increases in the direction defined from said central portion to said terminating edge (12c) of the second flat cable (12).

19. An ultrasonic diagnostic scanning probe comprising:
a housing having a longitudinal axis;
an ultrasonic transducer array having a longitudinal axis and a plurality of transducer elements positioned along said longitudinal axis of said ultrasonic transducer array for scanning in a scan plane extending through said longitudinal axis of said ultrasonic transducer array;
means for mounting said ultrasonic transducer array within said housing for pivotal movement of said ultrasonic transducer array about an axis extending along said longitudinal axis of said housing;
drive means for pivoting said ultrasonic transducer array;
a flat flexible cable having a plurality of electrical conductors individually connected to said transducer elements, said flexible flat cable extending substantially radially outward from said ultrasonic transducer array;
and means connected to said flexible flat cable for connecting said flexible flat cable to a utilization unit.

20. An ultrasonic diagnostic scanning probe comprising:
a substantially cylindrical housing having:
(a) a peripheral wall, and
(b) a longitudinal axis;
a multi-element ultrasonic transducer array formed of a plurality of transducer elements disposed side-by-side along an axis for emitting an ultrasonic beam in a plane extending through said axis of said multi-element ultrasonic transducer array;
means for mounting said multi-element ultrasonic transducer array within said housing with said axis of said multi-element ultrasonic transducer array extending along said longitudinal axis of said housing for rotation of said array about a rotation axis extending along said longitudinal axis of said housing;
drive means for rotating said multi-element ultrasonic transducer array about said rotation axis;
a flat flexible cable having a plurality of electrical conductors, one for each element of said multi-element ultrasonic transducer array, connected at one end to said transducer elements of said array and extending substantially radially outward from said array toward said peripheral wall of said housing;
and means connected to a second end of said flexible flat cable for connecting said flexible flat cable to a utilization unit.

* * * * *